United States Patent
Hosted, Jr. et al.

(10) Patent No.: US 7,220,567 B2
(45) Date of Patent: May 22, 2007

(54) **ISOLATION OF *MICROMONOSPORA CARBONACEA* VAR AFRICANA PMLP1 INTEGRASE AND USE OF INTEGRATING FUNCTION FOR SITE-SPECIFIC INTEGRATION INTO *MICROMONOSPORA HALOPHITICA* AND *MICROMONOSPORA CARBONACEA* CHROMOSOME**

(75) Inventors: Thomas J. Hosted, Jr., Summit, NJ (US); Ann C. Horan, Summit, NJ (US)

(73) Assignee: Schering Corporation, Kenilworth, NJ (US)

( * ) Notice: Subject to any disclaimer, the term of this patent is extended or adjusted under 35 U.S.C. 154(b) by 1097 days.

(21) Appl. No.: 09/855,340

(22) Filed: May 15, 2001

(65) Prior Publication Data

US 2002/0076788 A1 Jun. 20, 2002

Related U.S. Application Data

(60) Provisional application No. 60/204,670, filed on May 17, 2000.

(51) Int. Cl.
*C12N 1/21* (2006.01)
*C12N 15/00* (2006.01)
*C12N 15/74* (2006.01)
*C07H 21/04* (2006.01)

(52) U.S. Cl. .................. 435/252.3; 435/320.1; 435/471; 536/23.1; 536/23.7

(58) Field of Classification Search ............... 536/23.1, 536/23.4, 24.1; 435/235.1, 320.1, 471, 252.3
See application file for complete search history.

(56) References Cited

U.S. PATENT DOCUMENTS

| | | | |
|---|---|---|---|
| 5,688,689 A | 11/1997 | Smokvina et al. | |
| 5,741,675 A | 4/1998 | Friedmann et al. | |
| 6,861,513 B2 * | 3/2005 | Hosted et al. | 536/23.1 |
| 2004/0101832 A1 * | 5/2004 | Hosted et al. | 435/6 |

FOREIGN PATENT DOCUMENTS

EP 0403173 12/1990

OTHER PUBLICATIONS

Baltz, et al., (1996) Trends in Biotechnology 14 (7): 245-250.
Simoneau, et al., (1993) EMBL Database entry. Database accession No. L15239 XP002192421.
Simoneau, et al., (1993) Nucleic Acids Res. 21(21): 4967-4974.
Alegre et al., Cloning of Frankia species putative tRNA(Pro) genes and their efficacy for pSAM2 site-specific integration in *Streptomyces lividans*, Appl Environ Microbiol, vol. 60, No. 12, pp. 4279-4283 (Dec. 1994).
Bar-Nir et al., tDNA(ser) sequences are involved in the excision of *Streptomyces griseus* plasmid pSG1, Gene., vol. 122, pp. 71-76, (Dec. 1992).

Boccard et al., The integrated conjugative plasmid pSAM2 of *Streptomyces ambofaciens* is related to temperate bacteriophages, EMBO Journal, vol. 8, No. 3, pp. 973-980 (1989).
Boccard et al., Structural analysis of loci involved in pSAM2 site-specific integration in Streptomyces, Plasmid, vol. 21, pp. 59-70 (1989).
Brasch et al., Excisive recombination of the SLP1 element in *Streptomyces lividans* is mediated by Int and enhanced by Xis, Journal of Bacteriology, vol. 175, No. 10, pp. 3075-3082 (May 1993).
Brasch et al., Localization and nucleotide sequences of genes mediating site-specific recombination of the SLP1 element in *Streptomyces lividans*, Journal of Bacteriology, vol. 175, No. 10, pp. 3067-3074 (May 1993).
Brown et al., Characterization of the genetic elements required for site-specific integration of plasmid pSE211 in *Saccharopolyspora erythraea*, Journal of Bacteriology, vol. 172, No. 4, pp. 1877-1888 (Apr. 1990).
Brown et al., Characterization of the genes and attachment sites for site-specific integration of plasmid pSE101 in *Saccharopolyspora erythraea* and *Streptomyces lividans*, Molecular Gen Genet., vol. 242, pp. 185-193 (1994).
Brown et al., Site-specific integration in *Saccharopolyspora erythraea* and multisite integration in *Streptomyces lividans* of actinomycete plasmid pSE101, Journal of Bacteriology, vol. 170, No. 5, pp. 2287-2295 (May 1988).
Cohen et al., The integrated and free states of *Streptomyces griseus* plasmid pSG1, Plasmid, vol. 13, pp. 41-50 (1985).
Gabriel et al., The actinophage RP3 DNA integrates site-specifically into the putative tRNA(Arg)(AGG) gene of *Streptomyces rimosus*, Nucleic Acids Res., vol. 23, No. 1, pp. 58-63 (1995).
Hagege et al., Mode and origin of replication of pSAM2, a conjugative integrating element of *Streptomyces ambofaciens*, Molecular Microbiology, vol. 10, No. 4, pp. 799-812 (1993).
Hagege et al., Transfer functions of the conjugative integrating element pSAM2 from *Streptomyces ambofaciens*: Characterization of a kil-kor system associated with transfer, Journal of Bacteriology, vol. 175, No. 17, pp. 5529-5538 (Sep. 1993).
Katz et al., Site-specific recombination in *Escherichia coli* between the att sites of plasmid pSE211 from *Saccharopolyspora erythraea*, Molecular Gen. Genet., vol. 227, pp. 155-159 (1991).
Kuhstoss et al., Plasmid cloning vectors that integrate site-specifically in *Streptomyces* spp., Gene., vol. 97, pp. 143-146 (1991).
Kuhstoss et al., Analysis f the Integration function f the streptomycete bacteriophage phl C31, Journal f Molecular Biology, vol. 222, pp. 897-908 (1991).

(Continued)

*Primary Examiner*—Nancy Vogel
*Assistant Examiner*—Walter Schlapkohl

(57) ABSTRACT

Plasmid genes from *Micromonospora carbonacea* var. *africana* ATCC39149 pMLP1 have been isolated cloned, sequenced and functionally identified. These genes have been used to create vectors which integrate in a site-specific manner into the host chromosome of actinomycete species.

15 Claims, 5 Drawing Sheets

OTHER PUBLICATIONS

Kuhstoss et al., Site-specific integration in *Streptomyces ambofaciens*: Localization of integration functions in S. ambofaciens plasmid pSAM2, J urnal f Bacteriology, vol. 171, No. 1, pp. 16-23 (Jan. 1989).

Lai et al., Development of an Impr ved cloning vector and transformation system in Amyc latopsis mediterranei (*Nocardia mediterranei*), Journal of Antibiot.(Tokyo), vol. 51, No. 2, pp. 161-169 (1998).

Madon et al., Site-specific integration and excisi n of pMEA100 in *Nocardia mediterranei*, Mol Gen Genet., vol. 209, pp. 257-264 (1987).

Martin et al., Site-specific integration of the *Streptomyces* plasmid pSAM2 in *Mycobacterium smegmatis*, Molecular Microbiology, vol. 5, No. 10, pp. 2499-2502 (1991).

Matshushima et al., A Gene Cloning System for '*Streptomyces toyocaensis*', Microbiology, vol. 142, pp. 261-267(1996).

Mazodier et al., The chromosomal integration site of the *Streptomyces* element pSAM2 overlaps a putative tRNA gene conserved among actinomycetes, Mol Gen Genet., vol. 222, pp. 431-434 (1990).

Moretti et al., Isolation and characterization of an extrachromosomal element from *Nocardia mediterranei*, Plasmid, vol. 14, pp. 126-133 (1985).

Pernodet et al., Plasmids in different strains of *Streptomyces ambofaciens*: free and integrated form of plasmid pSAM2, Mol. Gen. Genet., vol. 198, pp. 35-41 (1984).

Raynal et al., Structure of the chromosomal insertion site for pSAM2: functional analysis in *Escherichia coli*, Molecular Microbiology, vol. 28, No. 2, pp. 333-342 (1998).

Seoane et al., Targets for pSAM2 integrase-mediated site specific integration in the *Mycobacterium smegmatis* chromosome, Microbiology, vol. 143, pp. 3375-3380 (1997).

Sezonov et al., KorSA from the *Streptomyces* integrative element pSAM2 is a central transcriptional repressor: Target genes and binding sites, Journal of Bacteriology, vol. 182, No. 5, pp. 1243-1250 (Mar. 2000).

Sezonov et al., Characterization of pra, a gene for replication control in pSAM2, the integrating element of *Streptomyces ambofaciens*, Molecular Microbiology, vol. 17, No. 3, pp. 533-544 (1995).

Simonet et al., Excision and integration of a self-transmissable replicon of *Streptomyces ambofaciens*, Gene., vol. 59, pp. 137-144 (1987).

Smokvina et al., Functional analysis of the *Streptomyces ambofaciens* element pSAM2, Plasmid, vol. 25, pp. 40-52 (1991).

Smokvina et al., Construction of a series of pSAM2-based integrative vectors for use in actinomycetes, Gene., vol. 94, No. 1, pp. 53-59 (1990).

Sosio et al., Excision of pIJ408 from the chromosome of *Streptomyces glaucescens* and its transfer into *Streptomyces lividans*, Mol Gen Genet., vol. 218, pp. 169-176 (1989).

Thyagarajan et al., Site-specific genomic integration in mammalian cells mediated by phage phiC31 integrase, Molecular and Cellular Biology, vol. 21, No. 12, pp. 3926-3934 (Jun. 2001).

Vogtii et al., The chromosomal integration site for the *Streptomyces* plasmid SLP1 is a functional tRNA(Tyr) gene essential for cell viability, Molecular Microbiology, vol. 6, No. 201, pp. 3041-3050 (1992).

Zhu et al., Amplification on the Amycolatopsis (Nocardia) mediterranei plasmid pMEA100: sequence similarities to actinomycete att sites, Plasmid, vol. 24, pp. 132-142 (1990).

* cited by examiner (a)
```
  1 TAGGGGAATCCACTCCGGAGAGACGCCCGGAGCAATCCGGAGCATGACGAGCAGGTCAGGTGGCCTGTTGACCCCTGACCAGGGCCC
 95 CGGTACGGGTTCAATTCCCATCAGTCACCCGGCAAGTGGATCTACTCCACAGCAGATCAGGCCCCTCCGAA
167 GAGGGGCCTGATGCGTCATAGGGGACAGGTAGGGAACTCAA
```

(b)
```
  1 TATTAGTCCGCACGCGCCGGCCCCGCCGGCCGGAGCCCCGAGCGGAGAGCGCATGGTGGCTGTAGCTCAGTTGGCAGAGCACGGGTT
 90 GTCGTGGGTTCAATTCCCATCAGTCACCCGTACACGAAGGCCCCTCCACTCGGAGGGGGCCTTCGGCGTTC
162 CTGAGGGTTCGCGGTCAGGCGGTCGGCTCGGCGTCGGGGGACTCGGCCCCGTCGGCGGGAGTGGCCTCGCGTCGGGGA
      A  T  P  E  A  S  P  S  E  A  G  D  A  P  T  A  E  A  D  P  S
    22▼
```

(c)
```
  1 TGGCCGGGGGTGTGGCTATTATTAGTCCGCACGCCGCCCGGCCGGAGCCCGGAGCGGAGCGCATGGTGGCTGTAGCTCAGTTGGCAGAGCACCG
                                                                        attB/attP left juncture
 92 GGTTGTGGTCCCGGTTGTCGTGGGTTCAATTCCCATCAGTCACCCGGCAAGTGGATCTACTCCACAGCAG
162 ATCAGGCCCCCTCCGAAGAGGGGGCCTGATGCGTCATAGGGGACAGGTAGGGAACTCAACCCCGGCTCCTTGCTCGGTC
```

(d)
```
  1 TAGGGGAATCCACTCCGGAGAGACGCCCGGAGCAATCCGGAGCATGACGAGCAGGTCAGGTGGCCTGTTGACCCCTGACCAGGGCCC
                                                                          attP/attB right juncture
 95 CGGTACGGGTTCAATTCCCATCAGTCACCCGTACACGAAGGCCCCTCCACTCGGAGGGGGCCTTCGGCGTT
167 CCTGAGGGTTCGCGGTCAGGCGGTCGGCTCGGCGTCGGGGGACTCGGCCCCGTCGGCGGGAGTGGCCTCGGCGTCGGGGA
      A  T  P  E  A  S  P  S  E  A  G  D  A  P  T  A  E  A  D  P  S
    22▼
```

(a)
1   TAGGGAATCCACTCCGGAGACGCCCGGAGCAATCCGGAGCATGACGGAGCAACCAGCAGGTCAGGTGGCCTGTTGACCCCCTGACCAGGGCCC
95  CGGTACGGGTTCAATTCCCATCAGTCACCCGGCAAGTGGATCTACTCCACAGCAGATCAGGCCCCCTCCGAA
167 GAGGGGGCCTGATGCGTCATAGGGGACAGGTAGGGGAACTCAA (b)
1   TTTCTCCGCACCCGCCCGGGGCGTTCGACCCGGTGCGGCGGCATGGCGGGGGTGCCGGTGCTGTAGCTCAGTTGGCAGAGCACCGGGTTGTGGTCCCGGT
90  TGTCGTGGGTTCAATTCCCATCAGTCACCCCAGGTAAGACCCAGGTCAGGGCCGGTTCTCACCGGCCCTGA
161 CGCATTTTCAGGGGCATGGTGGGGGCGCTACCGGGGGTGGGGTGTCTCACCGGAGCCAGCATCTGATCAGGCGATCGAGCCGGCGCTGCCGGG
        22◄ · R  P  H  P  T  E  G  R  A  L  M  E  I  L  R  D  L  R  R  Q  R (c)
1   TTTCTCCGCACCCGCCCGGGGCGTTCGACCCGGTGCGGCGGCATGGTGGCTGTAGCTCAGTTGGCAGAGCACCGGGTTGTGGTCCCGGT
                                                                      attB/attP left juncture
90  TGTCGTGGGTTCAATTCCCATCAGTCACCCGGCAAGTGGATCTACTCCACAGCAGATCAGGCCCCCTCCGAA
162 GAGGGGGCCTGATGCGTCATAGGGGACAGGTAGGGGAACTCAACCCCCGGCTCCTCCTTGCTCGGGTCATGCCGTCCGGTCACCCCTCCGCGT
257 ACCTGGCCCTCTCCGTTCCTGGATCTCGGCCGGCAGTGATCGCGGCAGGTGCGCCTCC (d)
1   TAGGGGAATCCACTCCGGAGACGCCCGGAGCAATCCGGAGCATGACGGAGCAACCAGCAGGTCAGGTGGCCTGTTGACCCCCTGACCAGGGCCCC
                                                                      attP/attB right juncture
96  GGTACGGGTTCAATTCCCATCAGTCACCCAGGTAAGACCCAGGTCAGGGCCGGTTCTCACCGGCCCTGACG
168 CATTTTCAGGGGCATGGTGGGGGCGCTACCGGGGGTGTCTCACCGGAGCCAGCATCTGATCAGGCGATCGAGCCGGCGCTGCCGGG
        22◄ · R  P  H  P  T  E  G  R  A  L  M  E  I  L  R  D  L  R  R  Q  R

ISOLATION OF *MICROMONOSPORA CARBONACEA* VAR AFRICANA PMLP1 INTEGRASE AND USE OF INTEGRATING FUNCTION FOR SITE-SPECIFIC INTEGRATION INTO *MICROMONSPORA HALOPHITICA* AND *MICROMONOSPORA CARBONACEA* CHROMOSOME

This application claims the benefit of U.S. Provisional Application No. 60/204,670 filed May 17, 2000.

FIELD OF THE INVENTION

The present invention relates generally to isolated nucleic acids and the creation of vectors for the study and expression of genes in actinomycetes. The invention more particularly relates to genes isolated from a *Micromonospora* lysogenic phage which can be used to create vectors for site-specific integration into *Micromonospora* chromosomes.

BACKGROUND

Actinomycetes are branched filamentous Gram-positive bacteria. *Streptomyces, Micromonospora, Nocardia, Actinoplanes, Saccharopolyspora, Actinomadura, Thermomonospora, Microbispora, Streptosporangium* and others all represent genera of the Actinomycetes (Atlas of Actinomycetes, Asakura Publishing Co., Ltd 1996). Actinomycetes are very important industrially because they produce a variety of secondary metabolites such as antibiotics, herbicides, anticancer agents, antihelmintics, and anabolic agents (Demain., Appl. Microbiol and Biotechnology., 1999, 52:455–463). Antibiotics are a large and complex group of chemical substances which exert deleterious effects on other organisms, many of which organisms are harmful to humans. Thus, antibiotics are particularly important secondary metabolites to study and produce. This is especially true because many pathogens can develop antibiotic resistance to known antibiotics.

Given the actinomycetes' proclivity for producing secondary metabolites such as antibiotics, it is especially advantageous to develop new tools such as vectors, promoters and the like to allow actinomycetes to be easily genetically manipulated. These tools would make it possible to control the levels of expression of genes encoding for secondary metabolites and also would make it possible to prepare derivatives or intermediates of these metabolites. In addition, the development of new vectors utilizing novel genes would make it possible to program microorganisms such as actinomycetes to produce recombinant products such as hybrid antibiotics via genetic engineering techniques.

Integrating vectors are vectors which integrate into a transformed host's chromosome rather than replicating autonomously. They are particularly useful in transforming actinomycetes because they allow for the especially efficient production of secondary metabolites because of their high transformation rates, site specific integrative capacity and stable maintenance in host chromosomes without antibiotic selection.

Vectors have been developed for use in actinomycetes that contain att/int functions for site-specific integration of plasmid DNA. The two systems available make use of the att/int functions of bacteriophage phiC31 (U.S. Pat. No. 5,190,870) and plasmid pSAM2 (U.S. Pat. No. 5,741,675). However, there is a need for additional vectors with att/int functions for site-specific integration in *M. carbonacea* and similar organisms.

The present inventors have responded to the above needs and have isolated genes from the actinomycete, *Micromonospora carbonacea* var. *africana* (ATCC39149, SCC1413) lysogenic phage pMLP1, in order to create vectors which can be used for site-specific integration into *Micromonospora* chromosomes. These integrating vectors can be used to express actinomycete genes, manipulate secondary metabolic pathways and create new metabolic products such as hybrid antibiotics.

SUMMARY OF THE INVENTION

The present invention provides novel polynucleotide sequences coding for integrase (int) and excisionase (xis) genes and an integrase attachment site (attP) isolated from pMLP1, a lysogenic phage isolated from *Micromonospora carbonacea* var. *africana* (ATCC39149, SCC1413). The invention also provides recombinant vectors comprising these genes as well as hosts transformed with these vectors and methods of transforming these hosts.

In one embodiment, the present invention provides isolated polynucleotides comprising sequences which are at least about ninety percent homologous to the nucleotide sequences set forth in SEQ ID NOS: 1–3. These isolated polynucleotides encode novel genes and DNA sequences involved in plasmid integration into a host chromosome. Specifically, these isolated sequences encode a site-specific integrase (int), an excisionase (xis), and an integrase attachment site (attP). In a preferred embodiment, the polynucleotides comprise sequences set forth in SEQ ID NOS: 1–3.

In addition, the invention provides isolated polynucleotides having a sequence at least about 90% homologous to SEQ ID NOS: 4–9, and preferably, having the nucleotide sequences set forth in SEQ ID NOS: 4–9. These sequences encode the *M. carbonacea* (attB) region (SEQ ID NO: 4) as well as the left and right juncture regions attB/attP (SEQ ID NO: 5) and attP/attB (SEQ ID NO: 6) regions formed when the attP site of pMLP1 is integrated into the attB site of *M. carbonacea*. In addition, these sequences encode the *M. halophitica* attB region (SEQ ID NO: 7), as well as the left and right juncture regions attB/attP (SEQ ID NO: 8) and attP/attB (SEQ ID NO: 9) formed when the attP site of pMLP1 is integrated into the (attB) site of *M. halophitica*.

In another embodiment, the present invention provides recombinant vectors comprising one or more nucleotide sequences which are at least about ninety percent homologous to the nucelotide sequences set forth in SEQ ID NOS: 1–3. In a preferred embodiment, the invention provides a recombinant vector comprising one or more of SEQ ID NOS: 1–3. In an especially preferred embodiment, that vector is an integrating vector capable of integrating into the chromosome of a host cell.

In yet another embodiment, the present invention provides host cells comprising the vectors of the instant invention. In a preferred embodiment, the host cell is bacterial. In an especially preferred embodiment, the host cell is an actinomycete such as a *Micromonospora*.

In a final embodiment, the invention provides a method for transforming an actinomycete with an integrating vector comprising a) isolating a polynucleotide having a sequence at least ninety percent homologous to a sequence selected from the group consisting of SEQ ID NOS: 1–3; b) inserting the polynucleotide or polynucleotides into a vector; and c) transforming an actinomycete such that the vector integrates into the actinomycete chromosome. Preferably the isolated polynucleotides have sequences selected from the group consisting of SEQ ID NOS: 1–3. Most preferably, the vector comprises SEQ ID NOS: 1–3.

BRIEF DESCRIPTION OF THE DRAWINGS

FIG. 4 Sequences of (a) pMLP1 attP (region containing the attP site) (SEQ ID NO: 10), (b) *M. carbonacea* attB region (nucleotide sequence) (SEQ ID NO: 4), (c) pSPRH840 attB/attP left juncture region (SEQ ID NO: 5), (d) pSPRH840 attP/attB right juncture region (nucleotide sequence) (SEQ ID NO: 6). Regions of attP, attB, and attB/attP sharing homology are indicated by bold larger sized font. (a), pSPRH840 attP site indicated by large bold font; (b), *M. carbonacea* attB site indicated by large bold font (nucleotide sequence). Arrows indicate: (a), attP (pSPRH840 attachment site); (b), *M. carbonacea* tRNA-His gene and attB site (nucleotide sequence); (c), pSPRH840 attB/attP tRNA-His gene; (d), pSPRH840 attP/attB 3' region of tRNA-His gene (nucleotide sequence). Inverted repeats are indicated by small arrows. The amino acid sequence in (b) and (d) is set forth in SEQ ID NO: 17.

FIG. 5: Sequences of (a) pMLP1 attP (region containing the attP site) (SEQ ID NO: 10), (b) *M. halophitica* attB region (nucleotide sequence) (SEQ ID NO: 7), (c) pSPRH840 attB/attP left juncture region (SEQ ID NO: 8), (d) pSPRH840 attP/attB right juncture region (nucleotide sequence) (SEQ ID NO: 9). Regions of attP, attB, attB/attP and attP/attB sharing homology are indicated by bold larger sized font. (a) pSPRH840 attP site indicated by large bold font; (b), *M. halophitica* attB site indicated by large bold font (nucleotide sequence). Arrows indicated: (a), attP (pSPRH840 attachment site); (b), *M. halophitica* tRNA-His gene and attB site (nucleotide sequence); (c), pSPRH840 attB/attP tRNA-His gene; (d), pSPRH840 attP/attB 3' region of tRNA-His gene (nucleotide sequence). k Inverted repeats are indicated by small arrows. The amino acid sequence in (b) and (d) is set forth in SEQ ID NO: 18.

DETAILED DESCRIPTION OF THE INVENTION

Figure 1:
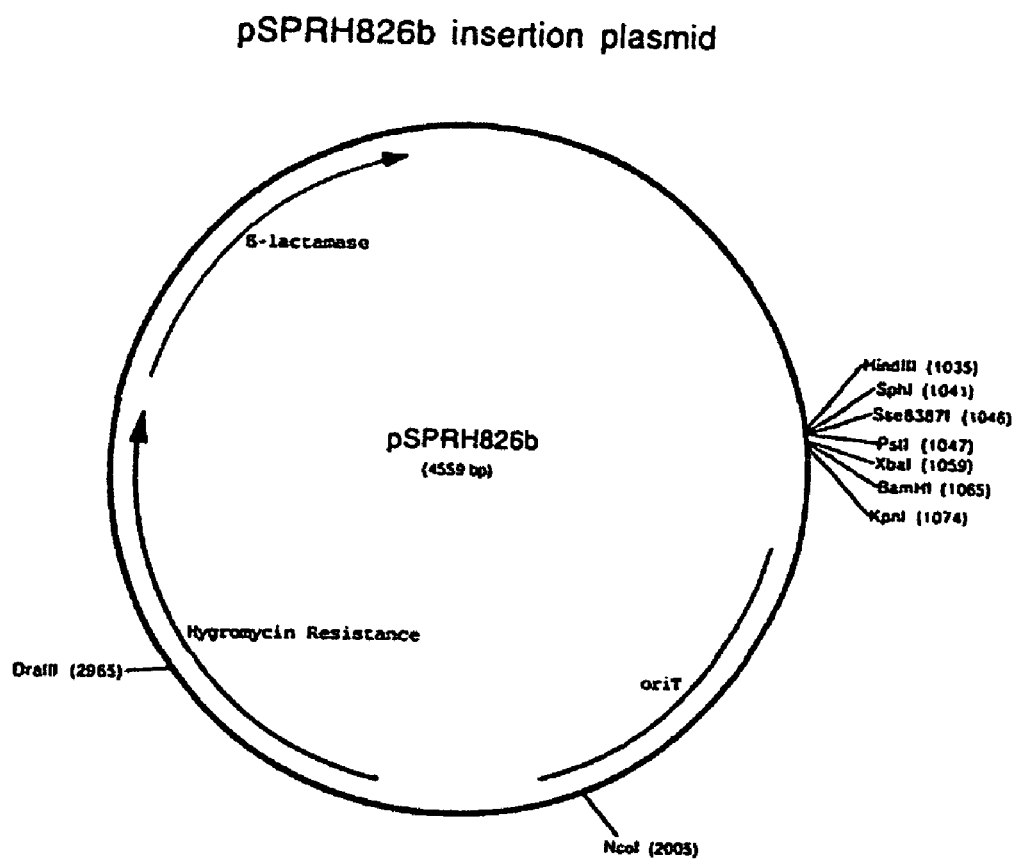
FIG. 1 is a schematic of plasmid pSPRH826b, an *E. coli-Micromonospora* insertion vector. β-lactamase, ampicillin resistance; hygromycin resistance; oriT, RK2 origin of transfer for conjugation. Restriction sites are indicated.

The present invention relates to nucleic acids isolated from bacteriophage (lysogenic phage) pMLP1 isolated from *Micromonospora carbonacea* var. *africana* ATCC39149. In addition, the invention relates to vector constructs made utilizing these nucleic acids. Specifically, these vector constructs can be utilized to integrate in a site-specific manner into the host chromosome of an actinomycete.

Before describing the invention in detail, the following definitions are provided to aid in an understanding of the specification and claims:

"Nucleic acid" or "polypeptide" as used herein refers to purine- and pyrimidine-containing or amino acid polymers of any length, either polyribonucleotides or polydeoxyribonucleotides or mixed polyribo-polydeoxyribo nucleotides. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases.

An "open reading frame" (ORF) as used herein is a region of a polynucleotide sequence that encodes a polypeptide; this region may represent a portion of a coding sequence or comprise a total coding sequence for the polypeptide.

A "coding sequence" or a "protein-coding sequence" is a polynucleotide sequence capable of being transcribed into mRNA and/or capable of being translated into a polypeptide. The boundaries of the coding sequence are typically determined by a translation start codon at the 5'-terminus and a translation stop codon at the 3'-terminus.

A "complement" of a nucleic acid sequence as used herein refers to the "antisense" sequence that participates in Watson-Crick base-pairing with the original sequence.

An "isolated" nucleic acid or polypeptide as used herein refers to a nucleic acid that is removed from its original environment such as, for example, from *Micromonospora carbonacea* plasmid pMLP1.

A nucleic acid or polypeptide sequence that is "derived from" a designated sequence refers to a sequence that corresponds to a region of the designated sequence. For nucleic acid sequences, this encompasses sequences that are homologous or complementary to the sequence, as well as "sequence-conservative variants" and "function-conservative variants." For polypeptide sequences, this encompasses "function-conservative variants." Sequence-conservative variants are those in which a change of one or more nucleotides in a given codon position results in no alteration in the amino acid encoded at that position. Function-conservative variants are those in which a given amino acid residue in a polypeptide has been changed without altering the overall configuration and function of the native polypeptide, including, but not limited to, replacement of an amino acid with one having similar physico-chemical properties (such as, for example, acidic, basic, hydrophobic, and the like). "Function-conservative" variants also include any polypeptides that have the ability to elicit antibodies specific to a designated polypeptide.

A "*M. carbonacea*-derived" nucleic acid or polypeptide sequence may or may not be present in other bacterial species, and may or may not be present in all *M. carbonacea* strains. This term is intended to refer to the source from which the sequence was originally isolated. An *M. carbonacea* plasmid-derived polypeptide, as used herein, may be used to search for homologous proteins in other species of bacteria or in eukaryotic organisms such as fungi and humans, etc.

A "probe" refers to a nucleic acid or oligonucleotide that forms a hybrid structure with a sequence in a target region due to complementarity of at least one sequence in the probe with a sequence in the target protein.

Nucleic acids are "hybridizable" to each other when at least one strand of nucleic acid can anneal to another nucleic acid strand under defined stringency conditions. Stringency of hybridization is determined, by the temperature at which hybridization and/or washing is performed and the ionic strength and polarity of the hybridization and washing solutions, as well as other parameters. Hybridization requires that the two nucleic acids contain substantially complementary sequences; depending on the stringency of hybridization, however, mismatches may be tolerated. The appropriate stringency for hybridizing nucleic acids depends on the length of the nucleic acids and the degree of complementarity, variables well known in the art.

"Gene" refers to a DNA sequence that encodes through its template or messenger RNA a sequence of amino acids characteristic of a specific peptide, polypeptide or protein. The term "gene" as used herein with reference to genomic DNA includes intervening, non-coding regions, as well as regulatory regions, and can include 5' and 3' ends.

"Gene sequence" refers to a DNA molecule, including both a DNA molecule which contains a non-transcribed or non-translated sequence. The term is also intended to include any combination of gene(s), gene fragment(s), non-transcribed sequence(s) or non-translated sequence(s) which are present on the same DNA molecule.

"Homologous nucleic acid sequences" are those which when aligned and compared exhibit significant similarities. Standards for homology in nucleic acids are either measures for homology generally used in the art by sequence comparison or based upon hybridization conditions, which are described in greater detail below. Nucleotide sequence homology is observed when there is identity in nucleotide residues in two sequences (or in their complementary strands) when optimally aligned to account for nucleotide insertions or deletions. Substantial homology also exists when one sequence will hybridize under selective hybridization conditions to another. Typically, selective hybridization will occur when there is at least about 55% homology over a stretch of at least about 30 nucleotides, preferably at least about 65% over a stretch of at least about 25 nucleotides, more preferably at least about 75%, and most preferably at least about 90% over about 20 nucleotides. See, e.g., Kanehisa, *Nucleic Acids Res.* 12:203 (1984).

The nucleotide sequences of the present invention may be derived from a variety of sources including DNA, cDNA, synthetic DNA, synthetic RNA or combinations thereof. Such sequences may comprise genomic DNA which may or may not include naturally occurring introns. Moreover, such genomic DNA may be obtained in association with promoter regions or poly (A) sequences. The sequences, genomic DNA or cDNA may be obtained in any of several ways. Genomic DNA can be extracted and purified from suitable cells by means well known in the art. Alternatively, mRNA can be isolated from a cell and used to produce cDNA by reverse transcription or other means.

"cDNA" refers to complementary or copy DNA produced from an RNA template by the action of RNA-dependent DNA polymerase (reverse transcriptase). Thus, a "cDNA clone" means a duplex DNA sequence complementary to an RNA molecule of interest, carried in a cloning vector or PCR amplified. This term includes genes from which the intervening sequences have been removed.

"Recombinant DNA" means a molecule that has been recombined by in vitro splicing of cDNA or a genomic DNA sequence.

"Cloning" refers to the use of in vitro recombination techniques to insert a particular gene or other DNA sequence into a vector molecule. In order to successfully clone a desired gene, it is necessary to use methods for generating DNA fragments, for joining the fragments to vector molecules, for introducing the composite DNA molecule into a host cell in which it can replicate, and for selecting the clone having the target gene from amongst the recipient host cells.

"Host" includes prokaryotes and eukaryotes. The term includes an organism or cell that is the recipient of a replicable expression vehicle.

An "integrating vector" is a vector capable of site-specific integration into a bacterial chromosome, and specifically into the attB site.

A "shuttle vector" is a vector capable of replication in *E. coli* and a second bacterial strain such as an actinomycete.

The methods traditionally used in molecular biology, such as preparative extractions of plasmid DNA, centrifugation of plasmid DNA in a cesium chloride gradient, agarose or acrylamide gel electrophoresis, purification of DNA fragments by electroelution, protein extractions with phenol or phenol/chloroform, ethanol or isopropanol precipitation of DNA in a saline medium, transformation in *Escherichia coli*, and the like, are well known to a person skilled in the art and are amply described in the literature. Maniatis T., et al., "Molecular Cloning, a Laboratory Manual," Cold Spring Harbor Laboratory, Cold Spring Harbor, N.Y., 1982; Ausubel F. M., et al., (eds), "Current Protocols in Molecular Biology," John Wiley & sons, New York 1987.

Protocols have been developed to genetically manipulate actinomycete genomes and biosynthetic pathways. These include the construction of *E. coli*-actinomycete shuttle vectors, gene replacement systems, transformation protocols, transposing mutagenesis, insertional mutagenesis, integration systems and heterologous host expression. These techniques are reviewed in numerous articles (Baltz et al., Trends Microbiol., 1998, 2:76–83, Hopwood et al., Genetic Manipulation of *Streptomyces:* A Laboratory Manual, 1985; Wohlleben et al., Acta Microbiol. Immunol. Hung, 1994, 41:381–9 [Review]).

The development of vectors for the genetic manipulation of actinomycetes began with the observation of plasmids in actinomycetes and the development of a transformation protocol of actinomycete protoplasts using polyethylene glycol (Bibb et al., Nature, 1980, 284:526–31). Many standard molecular techniques for *Streptomyces* were developed by Hopwood for *Streptomyces coelicolor* and *Streptomyces lividans* (Hopwood et al., Genetic Manipulation of *Streptomyces:* A Laboratory Manual, 1985). These techniques have been adapted and expanded to other actinomycetes.

Vectors incorporating antibiotic-resistance markers (AmR: apramycin; ThR: thiostrepton; SpR: spectinomycin) that function in *Streptomyces* and other features have allowed the development of vectors for (a) integration via homologous recombination between cloned DNA and *Streptomyces* chromosomes, (b) *E. coli*-actinomycete shuttle vectors, and (c) site-specific integration vectors utilizing att/int functions from bacteriophage phiC31 which integrates into the phiC31 attB site (U.S. Pat. No. 5,190,870) or att/int functions from pSAM2 which integrates into the pSAM2 attB site (U.S. Pat. No. 5,741,675), and (d) gene replacement vectors. Homologous recombination between the cloned DNA and the chromosome can be used to make insertional knockouts of specific genes. *E. coli*-actinomycete shuttle vectors can be used to introduce copies of genes into actinomycetes. Site-specific integration plasmids can be used to introduce heterologous genes into the actinomycete chromosome for complementation, expression studies and production of hybrid secondary metabolites.

Many actinomycetes contain restriction systems that limit the ability to transform organisms by protoplast transformation. More recent gene transfer procedures have been developed for introducing DNA into *Streptomycetes* by conjugation from *Escherichia coli*. This employs a simple mating procedure for the conjugal transfer of vectors from *E. coli* to Streptomyces species that involves plating of the donor strain and either germinated spores or mycelial fragments of the recipient strain. Conjugal plasmids contain the 760-bp oriT fragment from the IncP plasmid, RK2 and are transferred by supplying transfer functions in trans by the E. coli donor strain. Other recent developments that increase the frequency of recombination of non-replicating plasmids into the recipient actinomycete chromosome include transformation of non-replicating plasmids into protoplasts using denatured plasmid DNA (Oh and Chater, J. Bacteriol., 1997, 179:1227) and conjugation of non-replicating plasmids from a methyl minus strain of E. coli. (Smith et al., FEMS Microbiol. Lett., 1997, 155:2239).

Various strategies have been used to obtain gene replacements in Streptomycetes, for the construction of mutations and the modification of biosynthetic pathways (Baltz et al., 1998, supra; Hopwood et al., supra; Wohllenben et al., 1994, supra; Baltz and Hosted, TIBTECH, 1996, 14:245; Baltz, Curr. Op. Biotech., 1990, 1:1220). These methods have typically employed a two or three step procedure that results in allelic exchange. Initial crossover events between a non-integrating phage, non-replicating plasmid, or temperature sensitive plasmid and the Streptomycete chromosome are selected for by antibiotic resistance. Subsequent recombination events that result in gene replacement can be detected by screening the progeny of the initial recombinants by PCR analysis, Southern analysis, appearance of an expected phenotype or screening for the loss of a resistance marker which had previously been exchanged into the loci to be replaced. The last of these methods has been employed by Khosla et al., Mol. Microbiol., 1992, 6:323749; Khosla et al., J. Bacteriol., 1993, 175:2197204, to successfully modify the polyketide biosynthetic route of S. coelicolor. The strategy employed by Khosla et al., 1992, supra, also has the advantage of allowing placement of non-selectable and phenotypically silent alleles into chosen positions of the chromosome. Donadio et al., Proc. Natl. Acad. Sci. U.S.A., 1993, 90:711923 has also successfully reprogrammed the erythromycin pathway of Saccharopolyspora erythrae by gene replacement.

Non-replicating plasmids for gene replacement were initially utilized by Hilleman et al., Nucleic Acids Res., 1991, 19:72731, who used a derivative of pDH5 to construct mutations in the phosphinothricin tripeptide biosynthetic pathway of S. hygroscopicus. Plasmid-insertion events were obtained by thiostrepton selection, subsequent screening of the primary recombinants indicated that 4 of 100 isolates had undergone a double-crossover gene replacement.

Use of counterselectable or negative selection markers such as rpsL (confers streptomycin sensitivity) or sacB (confers sucrose sensitivity) have been widely employed in other microorganisms for selection of recombination that results in gene replacement. In S. coelicolor, Buttner utilized glk as a counterselectable marker in att minus phiC31 phage to select for recombination events to construct gene replacement mutants of three S. coelicolor RNA polymerase sigma factors (Buttner et al., J. Bacteriol., 1990, 172:336778). Hosted has developed a gene replacement system utilizing the rpsL gene for counterselection (Hosted and Baltz, J. Bacterial, 1997, 179:1806).

The construction of recombinant actinomycete strains to produce hybrid secondary metabolites has been accomplished (Baltz, Antibiotic Resistance and antibiotic development" Harvard Academic Publishers (in press). Current procedures use recombinant DNA techniques to isolate and manipulate secondary metabolic pathways and to express these pathways in surrogate hosts such as Streptomyces lividans. Heterologous expression of diverse pathways, polyketide, oligopeptide and β-lactam biosynthetic pathways, has been achieved. Furthermore, novel polyketide structures have been generated through the manipulation of polyketide genes forming chimeric pathways. Recently, novel polyketide modules have been isolated from environmental sources using PCR amplification and expressed in Streptomyces to yield novel chemical structures (Strohl et al., J. Industr. Microbiol., 1991, 7:163; Kim et al., J. Bacteriol., 1995, 77:1202; Ylihonko et al., Microbiology, 1996, 142:1965).

A number of Actinomycetes harbor integrative "elements" that contain att/int functions capable of directing site-specific recombination into the chromosome. These integrative elements include plasmids and bacteriophages which are often capable of transfer and integration into hosts devoid of the integrative-element. In some cases the integrative-element coexists a both a freely replicating and integrated form. Att/int regions characteristically consist of an excisionase (xis), integrase (int), and a short DNA region designated the attP element. The integrase acts as site-specific DNA recombinase that directs strand exchange recombination of the attP element with a chromosomal attB site. Often actinomycete attB sites are tRNA genes that share a short segment of identity with the attP element [Reiter et al., "Transfer RNA genes frequently serve as integration sites for prokaryotic genetic elements" Nucleic Acids Res 17(5):1907–14 (1989)] that extends from the anticodon loop to the 3' end of the tRNA gene. Recombination of the attP element with the attB site forms an attP/attB juncture (attL) that regenerates a functional tRNA gene and an attB/attP juncture (attR).

Actinomycetes integrative plasmids include Streptomyces ambofaciens ATCC23877 pSAM2 [Pemodet et al., "Plasmids in different strains of Streptomyces ambofaciens: free and integrated form of plasmid pSAM2" Mol Gen Genet 198(1):35–41 (1984)], Saccharopolyspora erythrea pSE21, Amycolytopsis mediteranei pMEA100 [Moretti et al., "Isolation and characterization of an extrachromosomal element from Nocardia mediterranei" Plasmid 14(2):126–33 (1985)], S. glaucescens pIJ408 S. coelicolor A3(2)SLP1 [Bibb et al., "Excision of chromosomal DNA sequences from Streptomyces coelicolor forms a novel family of plasmids detectable in Streptomyces lividans" Mol Gen Genet 184(2):230–40 (1981)], A. methanolitica pMEA300 [Vrijbloed et al., "A plasmid from the methylotrophic actinomycete Amycolatopsis methanolica capable of site-specific integration" J Bacteriol 176(22):7087–90 (1994)], and others. Actinomycete integrative bacteriophages include phiC-31, a broad host-range temperate streptomycete phage [Lomovskaya et al., "Characterization of temperate actinophage phi C31 isolated from Streptomyces coelicolor A3(2)" J Virol 9(2):258–62 (1972)], the S. rimosus RP2 and RP3 temperate phages [Rausch et al, "The temperate phages RP2 and RP3 of Streptomyces rimosus" J Gen Microbiol 139(Pt 10):2517–24 (1993)], and the VWB temperate phage from S. venezuelae [Van Mellaert et al., "Site-specific integration of bacteriophage VWB genome into Streptomyces venezuelae and construction of a VWB-based integrative vector" Microbiology 144(Pt 12):3351–8 (1998)]. The attB sites have been characterized for pSAM2, pSE211, RP3 and VWB and all correspond to the 3' end of a tRNA gene that shares a 58 bp to 112 bp segment of identity with the corresponding attP element. The conservation of tRNA genes at the sequence level often allows integration of these vectors into phylogeneticaly diverse hosts. This is exemplified by pSAM2 att/int function derived vectors which can integrate into numerous *Streptomyces* species [Simonet et al., "Excision and integration of a self-transmissible replicon of *Streptomyces ambofaciens*" *Gene* 59(1):137–44 (1987); Kuhstoss et al. "Site-specific integration in *Streptomyces ambofaciens*: localization of integration functions in *S. ambofaciens* plasmid pSAM2" *J Bacteriol* 171(1):16–23 (1989); Boccard et al., "Structural analysis of loci involved in pSAM2 site-specific integration in *Streptomyces*" *Plasmid* 21(1): 59–70 (1989)] and *Mycobacterium smegmatis* [Martin et al., "Site-specific integration of the *Streptomyces* plasmid pSAM2 in *Mycobacterium smegmatis*" *Mol Microbiol* 5(10):2499–502 (1991)].

The instant invention relates to the isolation and identification of novel genes from the *M. carbonacea* pMLP1 bacteriophage. These genes have been used to create vectors for site-specific integration into host chromosomes. Specifically, use of the pMLP1 att/int site-specific integration function will allow for increasing a given gene dosage and for adding heterologous genes that lead to the formation of new products such as hybrid antibiotics. This procedure has many advantages over methods involving autonomously replicating plasmids. In particular, replicating plasmids require selection to be maintained and control of plasmid copy number is difficult so that gene dosage cannot be controlled. pMLP1 derived vectors integrate as a single copy per chromosome.

Vectors comprising the site-specific integrating function of pMLP1 can be used to permanently integrate copies of the gene of choice into the chromosome of actinomycetes. Vectors lacking actinomycete origins of replication can only exist in their integrated form in actinomycetes. Integrated vectors are extremely stable which allows the gene copies to be maintained without antibiotic selective pressure. The site-specific nature of the integration allows analysis of the integrants.

I. Nucleic Acid Sequences

The present inventors have isolated novel genes from *M. carbonacea* bacteriophage pMLP1. Example 1 describes the construction of a *M. carbonacea* cosmid library and creation of plasmid pSPR150 which contains the *M. carbonacea* int, xis and attP sites.

EXAMPLE I

Construction of a *M. carbonacea* cosmid library and isolation of pSPR150 *M. carbonacea* chromosomal DNA was partially digested with Sau3A1 to yield DNA of ~40 kb in size, treated with alkaline phosphatase (Boehringer Mannheim Biochemicals), ligated to BamHI digested pSupercos II (Stratagene), and packaged with Gigapack II packaging extract (Stratagene). Packaged DNA was titred on *E. coli* XL1-Blue-MFR' (Stratagene) and individual cosmid clones were stored as an ordered array in 96 well microtitre plates. Primary screening filters were prepared using a 96-well dot blot apparatus. Twelve cultures from a row of microtitre wells were pooled, plasmid DNA was prepared, stored as mixed pools and bound to nylon filters (BioRad Zeta-probe GT). Secondary screening was performed on individual cosmid clones from microtitre wells by PCR or Southern analysis.

Degenerate PCR primers PR144 (5' TGCTTCGACGC-CATCARGG3') and PR145 (5'GTGGAAICCGC-CGAAKCCGC3') were designed to amplify polyketide synthetase type I genes (Hutchinson et al., *Annual Review of Microbiology*, 1995, 49:201–238). PCR primers PR144 and PR145 were used to amplify a 0.6 kb fragment from *M. carbonacea* chromosomal DNA. The 0.6 kb fragment was cloned into the pNOTA vector (5 Prime 3 Prime Inc., Boulder, Colo.) and sequence analysis of the insert revealed BLAST homology to polyketide type I genes. PCR analysis of the *M. carbonacea* cosmid library using PR144 and PR145 were used to isolate cosmid pSPR150. The 4 kb pSPR150 insert was sequenced and revealed numerous phage like genes including genes and DNA regions with homology to database integrases, excisionases and attP attachment sites.

After obtaining the complete sequence of a 4 kb fragment subcloned from pSPR150 from the Gene Inspector program (Textco, Inc. West Lebanon, N.H.) and BLAST analysis (Genetics Computer Group, Program Manual for the GCG Package, Version 7, Madison, Wis.) was used to analyze the sequence. This analysis revealed the int gene which showed homology to other integrases in the NRRL database. Specifically, the int gene had a BLAST score of 2.6e-31 to Mycobacterium phage Ms6 integrase (accession number AF030986). Analysis of the predicted attP site showed homology to the attP sites found in phage phiC31 and plasmid pSAM2. In addition, an excisionase (xis) gene was identified via BLAST homologies. Specifically, the xis had a BLAST score of 0.51 to the c2 bacteriophage excisionase (accession number X94331). While the genes and DNA regions isolated from pMLP1 share homologies with other streptomycete plasmid functions, phylogenetic analysis of the pMLP1 genes and DNA regions clearly indicate that the identified pMLP1 proteins and DNA regions represent novel *Micromonosporacea*-specific pMLP1 bacteriophage functions. Specifically these include novel genes or DNA regions involved in pMLP1 specific integration and excision (int, xis, attP site).

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optical alignment of sequences for comparison can be conducted, e.g., by the local homology algorithm of Smith and Waterman (1981) Adv. Appl. Math. 2:482, by the homology alignment algorithm of Needlman and Wunsch (1970) J. Mol. Biol. 48:443, by the search for similarity method of Pearson and Lipman (1988) Proc. Nat'l Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

An example of an algorithm that is suitable for determining percent sequence identity and sequence similarity is the BLAST algorithm, which is described Altschul, et al. (1990) J. Mol. Biol. 215:403–410. Software for performing BLAST analyses is publicly available through the National Center for Biotechnology Information (ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity X from it maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff (1989) Proc. Nat'l Acad. Sci. USA 89:10915) alignments (B) of 50, expectation (E) of 10, M=5, N=4, and a comparison of both strands.

In addition to calculating percent sequence identity, the BLAST algorithm also performs a statistical analysis of the similarity between two sequences (see, e.g., Karlin and Altschul (1993) Proc. Nat'l Acad. Sci. USA 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Novel genes and DNA regions from the *M. carbonacea* bacteriophage pMLP1 have been isolated. The sequences of the present invention include the specific nucleic acid sequences set forth in the Sequence Listing that forms a part of the present specification. For convenience, the sequences are designated SEQ ID NO: 1–SEQ ID NOS: 3. The invention encompasses each sequence individually, as well as any combination thereof.

The gene sequences of this invention (SEQ ID NOS: 1–3) encode for both proteins and non-translated DNA regions involved in pMLP1 integration and excision. These sequences all represent novel pMLP1 bacteriophage functions or regions. In addition, sequences of the invention include the *M. carbonacea* (attB) region (SEQ ID NO: 4) as well as the left and right juncture regions attB/attP (SEQ ID NO: 5) and attP/attB (SEQ ID NO: 6) regions formed when the attP site of pMLP1 is integrated into the attB site of *M. carbonacea*. Also, these sequences encode the *M. halophitica* attB region (SEQ ID NO: 7), as well as the left and right juncture regions attB/attP (SEQ ID NO: 8) and attP/attB (SEQ ID NO: 9) formed when the attP site of pMLP1 is integrated into the (attB) site of *M. halophitica*. Table 1 shown below lists isolated pMLP1 sequences and the pMLP1-*M. carbonacea* and pMLP1—*M. halophitica* attB/attP and attP/attB regions as well as their functions based on BLAST homologies.

TABLE 1

| GENE PRODUCT OR DNA REGION | SEQ ID NO. | FEATURE | BASE PAIRS |
|---|---|---|---|
| pMLP1 int | 1 | integrase | 1394–2572 |
| pMLP1 xis | 2 | excisionase | 963–1388 |
| pMLP1 attP site | 3 | attP site | 2691–2715 |
| *M. carbonacea* attB region | 4 | tRNA-His | 44–119 |
| | | attB site | 95–119 |
| | | IR1 | 124–137 |
| | | IR2 | 142–155 |

TABLE 1-continued

| GENE PRODUCT OR DNA REGION | SEQ ID NO. | FEATURE | BASE PAIRS |
|---|---|---|---|
| *M. carbonacea* attB/attP region | 5 | tRNA-His | 44–119 |
| | | attB/attP site | 95–119 |
| | | IR1 | 157–174 |
| | | IR2 | 179–198 |
| *M. carbonacea* attP/attB region | 6 | attP/attB site | 101–125 |
| | | IR1 | 130–143 |
| | | IR2 | 148–161 |
| *M. halophitica* attB region | 7 | tRNA-His | 45–121 |
| | | attB site | 96–121 |
| | | IR1 | 134–145 |
| | | IR2 | 150–161 |
| *M. halophitica* attB/attP region | 8 | attB/attp site | 96–120 |
| | | tRNA-His | 45–120 |
| | | IR1 | 140–158 |
| | | IR2 | 162–178 |
| *M. halophitica* attP/attB region | 9 | attP/attB site | 101–126 |
| | | IR1 | 139–150 |
| | | IR2 | 155–166 |

IR = Inverted Repeat

Although the exact sequences of the DNA sites, regions and functionalities are set out in SEQ ID NOS: 1–9, this invention also relates to slight variants of these sequences. Specifically, while the specific sequences are derived from pMLP1, and from *M. carbonacea* and *M. halohitica* transformed with nucleotide sequences derived from pMLP1, the invention encompasses sequences that are homologous or complementary to the sequences as well as sequence- and function-conservative variants to the sequences. Sequence-conservative variants are those in which a change of one or more nucleotides in a given codon position results in no alteration in the amino acid encoded at that position. Function-conservative variants are those in which a given amino acid residue in a polypeptide has been changed without altering the overall configuration and function of the native polypeptide, including, but not limited to, replacement of an amino acid with one having similar physico-chemical properties (such as, for example, acidic, basic, hydrophobic, and the like). Function-conservative variants also include any polypeptides that have the ability to elicit antibodies specific to a designated polypeptide.

In seeking to protect their invention, the novel sequences have been described in terms of specific sequences as well as those sequences sharing considerable homology to their sequences. Specifically, the invention is intended to include not only the exact polynucleotide sequences as set forth in SEQ ID. NOS: 1–9, but also to include polynucleotide sequences having at least about ninety percent homology to their novel isolated sequences. Preferably, the sequences of the instant invention share at least ninety-five percent homology to the sequences set forth in SEQ ID NOS: 1–9 and most preferably, share at least 98% homology to the sequences set forth in SEQ ID NOS: 1–9 including complete protein coding sequences and complements thereof.

Stringency of conditions employed in hybridizations to establish homology are dependent upon factors such as salt concentration, temperature, the presence of organic solvents, and other parameters. Stringent temperature conditions usually include temperatures in excess of about 30° C., often in excess of about 37° C., typically in excess of about 45° C., preferably in excess of about 55° C., more preferably in excess of about 65° C., and most preferably in excess of about 70° C. Stringent salt conditions will ordinarily be less than about 1000 mM, usually less than about 500 mM, more usually less than about 400 mM, preferably less than about 300 mM, more preferably less than about 200 mM, and most preferably less than about 150 mM. For example, salt concentrations of 100, 50 and 20 mM are used. The combination of the foregoing parameters, however, is more important than the measure of any single parameter. See, e.g., Wetmur et al., J. Mol. Biol. 31:349 (1968).

Vectors

The sequences of the invention may be used in any actinomycete into which the vectors of the invention are capable of integrating. For instance, the sequences of the invention may be incorporated into strains of *Streptomyces, Mycobacteria, Bacilli, Micromonospora* and the like. Strains such as *S. pristinaespiralis* (ATCC 256486), *S. antibioticus* (DSM 40868), *S. bikiniensis* (ATCC 11062), *S. parvulus* (ATCC 12434), *S. glauescens* (ETH 22794), *S. actuosus* (ATCC 25421), *S. coelicolor* (A3(2)), *S. ambofaciens, S. lividans, S. griseofuscus, S. limosus* are particularly useful in fermentation processes. (See also, *Smokldvina* et al., Proceedings, 1:403–407).

Vectors that can be used in this invention include microbial plasmids, viruses, bacteriophage, integratable DNA fragments, and other vehicles which may facilitate integration of the nucleic acids into the genome of the host. Plasmids are the most commonly used form of vector but all other forms of vectors which serve an equivalent function and which are, or become, known in the art are suitable for use herein. See, e.g., Pouwels et al., *Cloning Vectors: A Laboratory Manual*, 1985 and Supplements, Elsevier, N.Y., and Rodriguez et al. (eds.), *Vectors: A Survey of Molecular Cloning Vectors and Their Uses*, 1988, Buttersworth, Boston, Mass.

Expression of nucleic acids utilizing the vectors of this invention can be carried out by conventional methods. Strains of *E. coli* and various actinomycete strains such as *Streptomyces* and *Micromonospora* strains are particularly preferred.

The invention provides a site specific integrase gene and integration site and attachment site. (SEQ ID NOS: 1–3). Use of the att/int site-specific integration functions allows for increasing a given gene dosage and for adding heterologous genes that may lead to the formation of new products, such as hybrid antibiotics. This procedure has many advantages over methods involving autonomously replicating plasmids. In particular, att/int derived vectors integrate as a single copy per chromosome. Plasmids comprising the site-specific integrating functions allow integration of the gene of choice into the chromosome of actinomycetes. Integrated vectors are extremely stable which allows the gene copies to be maintained without antibiotic selection.

Plasmids comprising the site-specific integrating function of the invention can be used to permanently integrate copies of a heterologous gene of choice into the chromosome of many different hosts. The vectors can transform these hosts at a very high efficiency. Because the vectors do not have actinomycete origins of replication, the plasmids cannot exist as autonomously replicating vectors in actinomycete hosts. The plasmids only exist in their integrated form in these hosts. The integrated form is extremely stable which allows the gene copies to be maintained without antibiotic selective pressure. The result is highly beneficial in terms of cost, efficiency, and stability of the fermentation process.

Advantageously, the integrative vectors derived from this novel recombinant DNA sequence coding for a desired product, including but by no means limited to, an actinomycete gene. The product can be a peptide, polypeptide or protein of pharmaceutical or agri- foodstuffs importance. One can increase the copy number of the product's sequence per cell, and hence increase the levels of production of a given product. One may also create integrative vectors utilizing the att/int genes of the invention to block the biosynthesis of a metabolite, or to produce derivatives of the metabolite.

In addition to using integrating vectors to integrate genes which increase the yield of known products or generate novel products, such as hybrid antibiotics or other novel secondary metabolites, vectors can also be used to integrate antibiotic resistance genes into strains in order to carry out bioconversions with compounds to which the strain is normally sensitive. The resulting transformed hosts and methods of making the antibiotics are within the scope of the present invention.

Prokaryotic expression control sequences typically used include promoters, including those derived from the β-lactamase and lactose promoter systems [Chang et al., *Nature* 198:1056 (1977)], the tryptophan (trp) promoter system [Goeddel et al., *Nucleic Acids Res.* 8:4057 (1980)], the lambda $P_L$ promoter system [Shimatake et al., *Nature* 292:128 (1981)] and the tac promoter [De Boer et al., *Proc. Natl. Acad. Sci. USA* 292:128 (1983)]. Numerous expression vectors containing such control sequences are known in the art and available commercially.

Those skilled in the art will readily recognize that the variety of vectors which can be created utilizing the genes of the invention is virtually limitless. The only absolute requirement is that the plasmid comprise an origin of replication which functions in the host cell in which constructions are made, such as *E. coli* or *Bacillus*. No actinomycete origin of replication is required. In fact, in a specific embodiment the plasmid comprising the integrase comprises no actinomycete origin of replication. Other features, such as an antibiotic resistance gene, a multiple cloning site and cos site are useful but not required. A description of the generation and uses of cosmid shuttle vectors can be found in Rao et al., (Methods in Enzymology, 1987, 153:166198). In short, any plasmid which comprises the integrase is within the scope of this invention.

EXAMPLE II

Construction of *E. coli-Micromonospora* Insertion Vector pSPRH826b and Integration Vector pSPRH840

The pSPRH826b insertion vector (FIG. 1) was constructed as follows. A 1.1 kb NruI/NotI fragment containing HmR from p16R1 (Garbe et al., *Microbiology*, 1994, 140:133–138) was treated with T4 polymerase to and ligated to SspI digested, T4 DNA polymerase treated pUC19 to yield pSPRH825. A 787 bp PstI fragment from pRL1058 (oriT region) was treated with T4 polymerase and ligated to NdeI digested, T4 DNA polymerase treated pSPRH825 to yield pSPRH826b.

Figure 2:
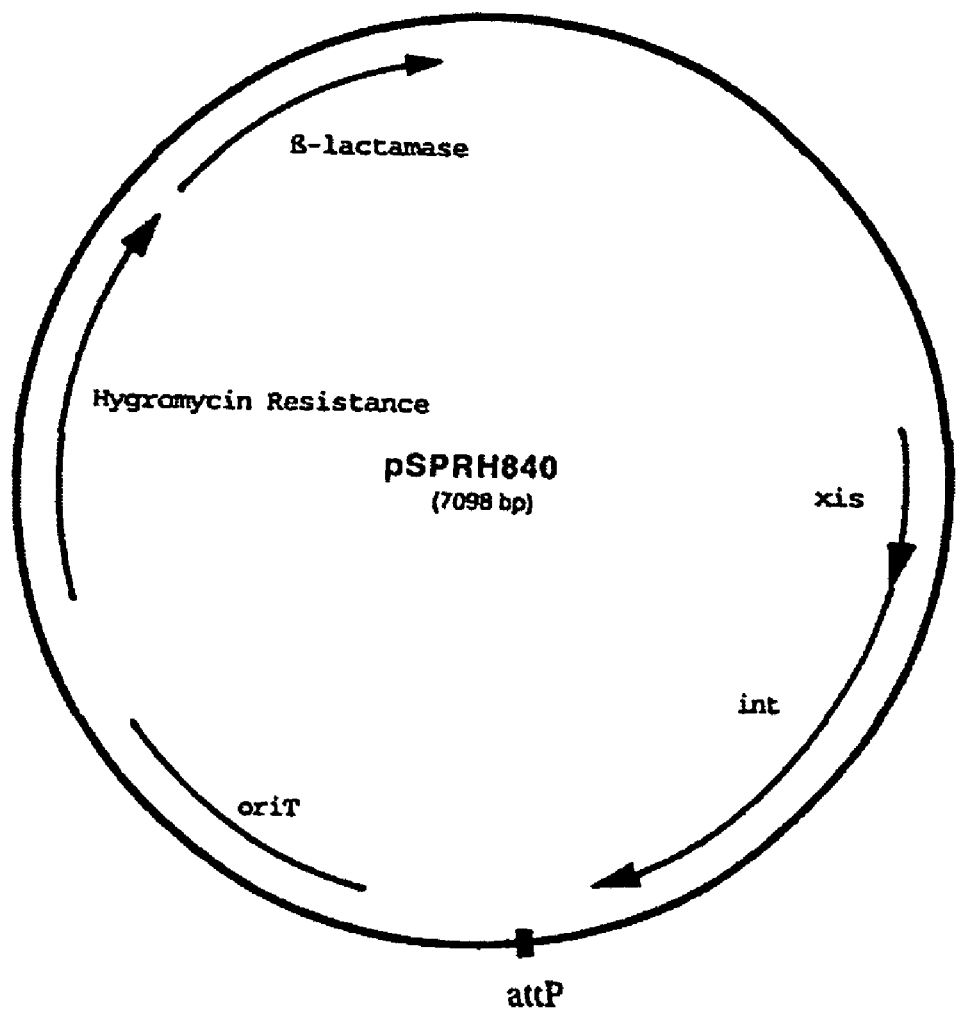
FIG. 2 is a schematic of plasmid pSPRH840, which was constructed by inserting the xis, int and attP regions from pMLP1 into backbone pSPRH826b. β-lactamase, ampicillin resistance; hygromycin resistance; oriT, RK2 origin of transfer for conjugation; xis, excisionase; int, integrate; attP: attachment site.

The pSPRH840 integrating vector (FIG. 2) was constructed as follows. A 4.0 kb KpnII fragment from cosmid pSPR150 containing the *M. carbonacea* pMLP1 xis, int, and attP region was ligated with BamHI cleaved pBluescriptII KS (Stratagene, LaJolla, Calif.) to yield pSPRH819. Sequence analysis of the 4.0 kb, KpnI fragment from the cosmid revealed the presence of an integrase gene designated int, an excisionase gene designated xis, and an integrase attachment site designated attP (SEQ. ID NOS: 1–3). A 2.5 kb NruI to XhoI fragment from pSPR819 was treated with T4 polymerase, alkaline phosphatase treated and ligated to pCRTopo 2.1 vector (Invitrogen Corp, Carlsbad Calif.) to yield pSPRH853. A 2.6 kb KpnI to PstI fragment from pSPRH853 was ligated to KpnI and PstI digested pSPR826b (FIG. 1) to yield pSPRH840 (FIG. 2).

EXAMPLE III

Transformation and Integration of pSPRH840 into M. carbonacea var africana ATCC39149 and M. halophytica SCC760

The plasmid pSPRH840 was transformed into Micromonospora carbonacea var. africana ATCC39149 and M. halophitica SCC760 as described in detail as follows.

Micromonospora carbonacea var. africana ATCC39149 and M. halophitica SCC760 were transformed with pSPRH840 (FIG. 2) by conjugation from E. coli S17-1 (Mazodier et al., Journal of Bacteriology, 1989, 6:3583–3585) to M. carbonacea and M. halophitica. E. coli S17-1 containing pSPR840 was grown overnight at 37° C. in LB supplemented with 100 ug/ml Ampicillin (Amp). The culture was inoculated into LB containing 10 ug/ml Amp at an 1:50 ratio and grown with shaking at 37° C. to an $OD_{600}$ of 0.4 to 0.5. Cells were harvested by centrifugation and washed three times with fresh LB lacking Amp. M. carbonacea and M. halophitica were grown separately in TSB medium at 30° C. with shaking to stationary phase. E. coli S17-1 containing pSPRH840 prepared as described above was mixed separately with M. carbonacea and M. halophitica in a total volume of 100 ul plated on AS1 plates using a plastic hockey spreader. Plates were incubated 15 hr at 29° C. and then overlaid with 50 ug/ml naladixic acid and 200 ug/ml hygromycin for selection. Transconjugants appearing in 2–3 weeks were picked, homogenized and grown in TSB media with 50 ug/ml-naladixic acid and 200 ug/ml hygromycin.

Transconjugants appearing in two to three weeks were picked, homogenized, and grown in TSB medium supplemented with 50 μ/ml naladizic acid and 200 μ/ml hygromycin. DNA was prepared from M. carbonacea transconjugant strains SPH201, SPH202, and SPH207 cleaved with KpnI, separated by gel electrophoresis, a Southern blot prepared, and probed with radiolabled pSPRH819 4.4 kb KpnI insert. Southern hybridization analysis confirmed the presence of a 3.0 kb hybridizing fragment in M. carbonacea strains SPH201, SPRH202 and SPRH207 and hybridizing fragments in M. halophitica strains transconjugant SPH206, SPH208, and SPH213. Southern analysis of parental M. carbonacea showed hybridization to a predicted 4.4 kb KpnI fragment from the replicating pMLP1 phage and 3.5 kb chromosomal fragment. The 3.5 kb hybridizing fragment indicates that pMLP1 is also integrated into the M. carbonacea chromosome. M. carbonacea strains SPH201, SPRH202 and SPRH207 lacked both freely replicating pMLP1 and integrated pMLP1 hybridizing fragments indicating that pMLP1 and integrated pMLP1 are cured from these strains.

Figure 3:
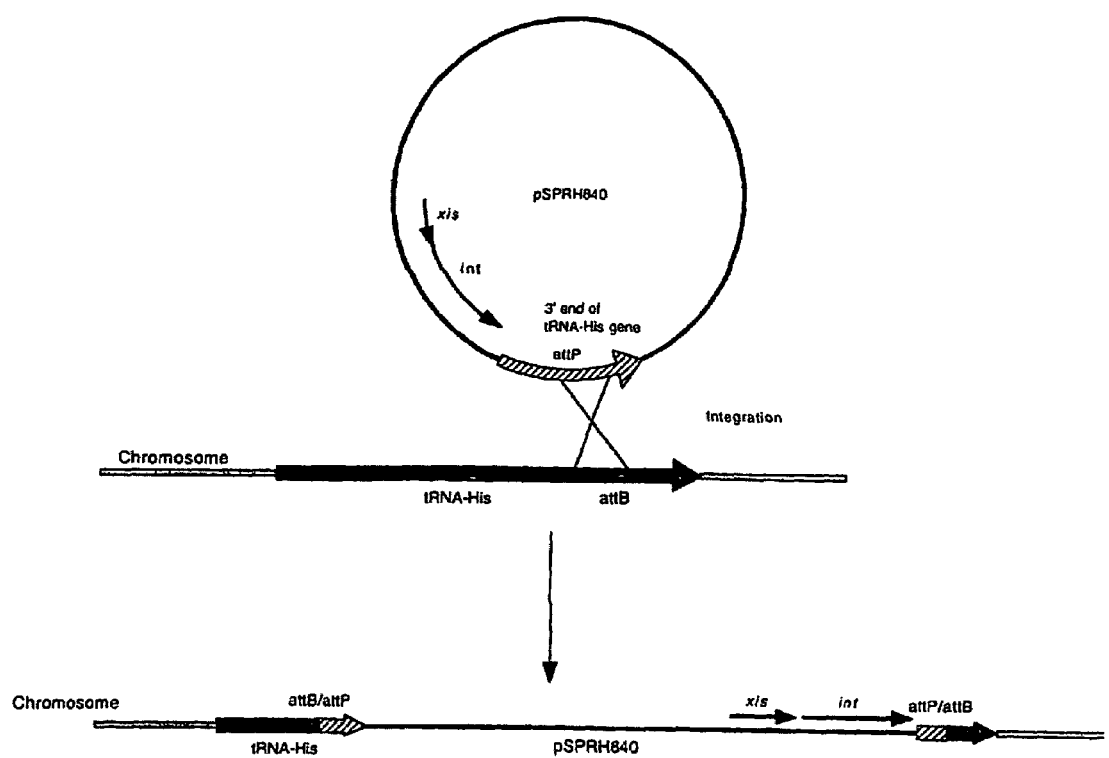
FIG. 3 is a schematic representation of pSPRH480 integration into attB (tRNA-His) located at the 3' end of the tRNA-His gene. xis, excisionas int, integrase; attP, attachment site pSPRH840 indicated by crosshatches; attB attachment site chromosome indicated by a solid black line; tRNA-His, transfer RNA histidine; attB/attP, left integration juncture; attP/attB, right integration juncture.

The integration of pSPRH840 into the M. carbonacea or M. halophitica chromosome forms an attB/attP left juncture and an attP/attB right juncture region (FIG. 3, FIG. 4, FIG. 5). These regions were cloned by digesting pSPRH840 integrant strain chromosomal DNA with PstI or KpnI, ligating digested DNA and transforming E. coli XL10 (Stratagene, LaJolla, Calif.). E. coli transformants were isolated, plasmid DNA prepared and analyzed by digestion and gel electrophoresis. Plasmids pSPRH873-13 and pSPRH870-1 were identified that contained the M. carbonacea attB/attP and attP/attB right juncture regions (FIGS. 4c, 4d). Plasmids pSPRH871-7 and pSPRH872-10 were identified that contained the M. halophitica attB/attP left and attP/attB right juncture regions (FIGS. 5c, 5d).

The attB/attP left and attP/attB right juncture regions formed during pSPRH840 integration in M. carbonacea and M. halophitica pSPRH840 integrants were sequenced (FIGS. 4c, 4d, FIGS. 5c, 5d). Analysis confirmed integration of pSPRH840 into the M. carbonacea chromosome, specifically into an attB site (bp 95 to bp 119, FIG. 4b) located at the 3' end of a tRNA-His gene (bp 44 to bp 119, FIG. 4b). The attP site (bp 101–125, FIG. 4a) and the attB site (bp 95–119, FIG. 4b) share perfect homology with each other. During integration an integrative crossover occurs between attP located on pSPRH840 and attB located on the M. carbonacea chromosome. This integrative crossover event creates two regions which contain an attB/attP site (bp 95–119, FIG. 4c) and an attP/attB site (bp 101–125, FIG. 4d). The attB/attP and attP/attB sites share perfect homology with the attP and attB sites. The M. carbonacea attB/attP left juncture region is illustrated in FIG. 4c. 5' DNA regions originate from the chromosomal attB region (FIG. 4b) and 3' DNA (apparent from bp 137 onward originate from the pSPRH840 attP region (FIG. 4a). The attB/attP left juncture region forms a new functional full length tRNA-His gene (bp 62 to bp 137, FIG. 4c) and an attB/attP site (bp 95–119, FIG. 4c). The M. carbonacea attP/attB right juncture region is illustrated in FIG. 4d. 5' DNA originates from the attP region (FIG. 4a) and 3' DNA (apparent from bp 125 onward) originate from the attB region (FIG. 4b). This attP/attB right juncture region forms an attP/attB site (bp 101 to bp 125, FIG. 4d) which is a truncated form of tRNA-His containing only the 3' end of the tRNA-His gene.

Analysis also confirmed integration of pSPRH840 into the M. halophitica chromosome, specifically into an attB site (bp 96 . . . 120, FIG. 5b) located at the 3' end of a tRNA-His gene (bp 45 . . . 120, FIG. 5b). The attP site (bp 101 . . . 125, FIG. 5a) and the attB site (bp 96 . . . 120, FIG. 5b) share perfect homology with each other. During integration an integrative crossover occurs between attP located on pSPRH840 and attB located on the M. halophitica chromosome. As is true for the M. carbonacea integrants, this integrative crossover event creates two regions which contain an attB/attP site (bp 96 . . . 120, FIG. 5c) and an attP/attB site (bp 101 . . . 125, FIG. 5d) As is true for M. carbonacea, the attB/attP and attP/attB sites share perfect homology with the attP and attB sites. The M. halophitica attB/attP left juncture region is illustrated in FIG. 5c. 5' DNA regions originate from the chromosomal attB region (FIG. 5b) and 3' DNA (apparent from bp 120 onward) originate from the pSPRH840 attP region (FIG. 5a). The attB/attP left juncture region forms a new functional full length tRNA-His (bp 45 . . . 120, FIG. 5c) and an attB/attP site (bp 96 . . . 120, FIG. 5c). The M. halophitica attP/attB right juncture region is illustrated in FIG. 5d. 5' DNA originates from the attP region (FIG. 5a) and 3' DNA (apparent from bp 125 onward) originate from the attB region (FIG. 5b). This attP/attB right juncture region forms an attP/attB site (bp 101 . . . 125, FIG. 5d) which is a truncated form of tRNA-His containing only the 3' end of the tRNA-His gene.

PCR primers PDH504 (5' AGGGCAACAAGG-GAAGCGTC 3') (SEQ ID NO: 13) and PDH505 (5' GGCGGGGGTGTGGCTATTATT 3') (SEQ ID NO: 14) were designed to amplify the attB region from M. carbonacea. PCR amplification of M. carbonacea chromosomal DNA yielded a fragment with homology to tRNA-His (bp 45 . . . 119, FIG. 4b). Contained within this tRNA-His gene, at the 3' end, is the M. carbonacea attB site (bp 95 . . . 119, FIG. 4b) that has perfect homology to the pMLP1 attP site (bp 101 . . . 125, FIG. 4a). PCR primers PDH 502 (5' TTGTTGGTCCGGCCCGCAACG 3') (SEQ ID NO: 19) were designed to amplify the attB region from *M. halophitica*. PCR amplification of *M. halophitica* chromosomal DNA yielded a fragment with homology to tRNA-His (bp 45 . . . 120, FIG. 5b). Contained within this tRNA-His gene, at the 3' end, is the *M. halophitica* attB site (bp 96 . . . 121, FIG. 5b) that has perfect homology to the pMLP1 attP site (bp 101 . . . 125, FIG. 5a).

While the present invention has been described with reference to one or more particular embodiments, those skilled in the art will recognize that many changes may be made thereto without departing from the spirit and scope of the present invention. each of these embodiments and obvious variations thereof is contemplated as falling within the spirit and scope of the claimed invention, which is set forth in the following claims.

The invention claimed is:

1. An isolated polynucleotide comprising the nucleotide sequence of SEQ ID NO: 2.

2. A recombinant vector comprising the polynucleotide of claim 1.

3. A recombinant vector comprising SEQ ID NOS: 1, 2 and 3.

4. The recombinant vector of claim 2, wherein said vector is an integrating vector.

5. The recombinant vector of claim 3, wherein said vector is an integrating vector.

6. A host cell comprising the vector of claim 2.

7. A host cell comprising the vector of claim 3.

8. The host cell of claim 6, wherein said host cell is bacterial.

9. The host cell of claim 8, wherein said host cell is an actinomycete.

10. The host cell of claim 9, wherein said host cell belongs to the genus *Micromonospora*.

11. The host cell of claim 7, wherein said host cell is an actinomycete.

12. The host cell of claim 11, wherein said actinomycete belongs to the genus *Micromonospora*.

13. An isolated polynucleotide comprising the nucleotide sequence of SEQ ID NO: 6.

14. A method for transforming an actinomycete with the vector of claim 6 comprising the step of contacting said actinomycete with said vector under conditions permitting transformation of said actinomycete.

15. The method of claim 14, wherein said vector comprises a promoter.

* * * * *

UNITED STATES PATENT AND TRADEMARK OFFICE
CERTIFICATE OF CORRECTION

PATENT NO. : 7,220,567 B2  Page 1 of 1
APPLICATION NO. : 09/855340
DATED : May 22, 2007
INVENTOR(S) : Hosted, Jr. et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (1097) days Delete the phrase "by 1097" and insert -- by 924 days --

Signed and Sealed this

Twenty-fifth Day of December, 2007

JON W. DUDAS
*Director of the United States Patent and Trademark Office*

UNITED STATES PATENT AND TRADEMARK OFFICE
CERTIFICATE OF CORRECTION

PATENT NO. : 7,220,567 B2 Page 1 of 1
APPLICATION NO. : 09/855340
DATED : May 22, 2007
INVENTOR(S) : Hosted, Jr. et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) (1097) days Delete the phrase "by 1097" and insert -- by 924 days --

Signed and Sealed this

First Day of January, 2008

JON W. DUDAS
*Director of the United States Patent and Trademark Office*

SEQUENCE LISTING

<160> NUMBER OF SEQ ID NOS: 9

<210> SEQ ID NO 1
<211> LENGTH: 1179
<212> TYPE: DNA
<213> ORGANISM: Micromonospora carbonacea

<400> SEQUENCE: 1

```
gtgtggatcg agaagaacgg gcccgtctac cgcattcggg acctcgttcg cggtaaaaag      60
gtcaccattc agaccggtta tccgacgaag accagcgcca agaatgcgat ggtgcagttc     120
cgtgcggagc agttgcaggg caacgcgctc atgccgcgcg gcggtcagat taccctcgcc     180
gatttcgtgg gggagtggtg gccgagctac gaaaagacgc tgaaaccgac cgccgtgaac     240
tcggagggca accggatccg caaccacctc ctgcccatac tcggccatct caccctttgac     300 gagctggacg ggcaggtcac ccagcagtgg gtcaacgacc tggaggccgg cgtcggcccg     360
tggccggagt ccacgcgggg tcgtcggaag ccgctggcag cgaagacgat cagcaactgc     420
cacggcctgc tgcacacgat ctgcggcgcg gcgatcgcg cgaaacggat caggctcaac      480
ccgtgctctt cgacgatgct gccccggcgc gagccgaaag agatgaagtt cctgagcgac     540
ccggagatcg gtcggcttat cacggcgctt ccgccgcact ggcgaccgct cgtcatgctg     600
ctggtggcga ccggtctgag gtggggtgag gcgatcggcc tgcgcgccgg ccgggtcgac     660
ctgctcgccg cgcggccccg gctgaccgtc gtcgagcagc tccaggagct ggccagcacg     720
ggagagctcg tcttccagtc gccgaagacc gcgaagggcc ggcgcacggt cagtttcacc     780
acgaaagtcg ctctactgct tacgccactc atcgccggaa agaaaagtga cgaggtcgtg     840
ttcaccgcgc cgaaaggcgg gatggtaagg acgcgcaatt tccggcggat ctgggtcaag     900
gcgtgcgagg aagcggggct tccgggctta cgcattcacg atctgcggca cactcacgcg     960
gcgatcctga tttctgccgg gcgtccgctg tcggcgatct cccgccgcct cggtcactcg    1020
tcgatcgcgg tcacggatct gctgtacggg cacctgcgtg aggaggtcga cgagggatc     1080 ctcgcggcga tcgaggaggc gatggccggc gtccgggctg aggacctgga ggcggaactc    1140
gacgaggagc tgacggacgt gttggccgac gcagcatga                           1179
```

<210> SEQ ID NO 2
<211> LENGTH: 426
<212> TYPE: DNA
<213> ORGANISM: Micromonospora carbonacea

<400> SEQUENCE: 2

```
atgcgcaaca caccgggggct ggggcgcggc acatgggccg catacgtcct caccgcccgc       60
gagcgcgccg gactgaccaa gagcgagttg gccaggcgca tccagaagga ccgggccacc      120
gtcggccggt gggaggacgg caagaaccgg cccgacgacg cggacctcgt tgcccgcgtc      180
```

```
gcccaggtgc tcggcctcga cctcgacgaa gccctcgccg ccgcaggtct gcgccccggc    240
gtcaccccgc cagcgacccc aaccatggac ctggacgagg aaatcgagct ggtccgcacc    300
gaccccaagc tggacgagga catgaagcgg cgcatcatcg ccctaatcct ggagcgccgt    360
gagcgcgaca aggcggcggc gatcgaggaa accaagcggc tcatcgacct gttccgccgg    420
agctga                                                               426

<210> SEQ ID NO 3
<211> LENGTH: 34
<212> TYPE: DNA
<213> ORGANISM: Micromonospora carbonacea

<400> SEQUENCE: 3
ccccggtacg ggttcaattc ccatcagtca cccg                                 34

<210> SEQ ID NO 4
<211> LENGTH: 241
<212> TYPE: DNA
<213> ORGANISM: Micromonospora carbonacea

<400> SEQUENCE: 4
tattagtccg cacgccgccc ggccccgccg gagcggagcg catggtggct gtagctcagt    60
tggcagagca ccgggttgtg gtcccggttg tcgtgggttc aattcccatc agtcacccgt    120
acacgaaggc cccctccact cggaggggc cttcggcgtt cctgagggtt cgcggtcagg    180
cggtcggctc ggcgctgggg gactcggccc cgtcggcggg agtggcctcg gcgtccgggg    240
a                                                                    241

<210> SEQ ID NO 5
<211> LENGTH: 243
<212> TYPE: DNA
<213> ORGANISM: Micromonospora carbonacea

<400> SEQUENCE: 5
tggcgggggt gtggctatta ttagtccgca cgccgcccgg ccccgccgga gcggagcgca    60
tggtggctgt agctcagttg gcagagcacc gggttgtggt cccggttgtc gtgggttcaa    120
ttcccatcag tcaccggca agtggatcta ctccacagca gatcaggccc ctccgaaga    180 ggggcctga tgcgtcatag gggacaggta ggggaactca accccggct ccttgctcgc    240 gtc                                                                  243

<210> SEQ ID NO 6
<211> LENGTH: 247
<212> TYPE: DNA
<213> ORGANISM: Micromonospora carbonacea

<400> SEQUENCE: 6 tagggaatc cactccggag acgcccggag caatccggag catgacggag caaccagcag    60
gtcaggtggc ctgttgaccc cctgaccagg gccccggtac gggttcaatt cccatcagtc    120
acccgtacac gaaggccccc tccactcgga gggggccttc ggcgttcctg agggttcgcg    180
gtcaggcggt cggctcggcg ctggggact cggccccgtc ggcgggagtg gcctcggcgt    240
ccgggga                                                              247

<210> SEQ ID NO 7
<211> LENGTH: 255
<212> TYPE: DNA
```

```
<213> ORGANISM: Micromonospora halophytica

<400> SEQUENCE: 7
tttctccgca cccgcccggg gcgttcgacc gggtgcggcg gcatggtggc tgtagctcag      60
ttggcagagc accggttgt ggtcccggtt gtcgtgggtt caattcccat cagtcacccc     120
aggtaagacc caggtcaggg ccggttctca ccggccctga cgcattttca ggggcatggt    180
gggggcgcta ccggggggtgg ggtgtctcac cgcgagccag catctcgatc aggcgatcga    240
gccggcgctg ccggg                                                     255

<210> SEQ ID NO 8
<211> LENGTH: 315
<212> TYPE: DNA
<213> ORGANISM: Micromonospora halophytica

<400> SEQUENCE: 8
tttctccgca cccgcccggg gcgttcgacc gggtgcggcg gcatggtggc tgtagctcag      60
ttggcagagc accggttgt ggtcccggtt gtcgtgggtt caattcccat cagtcacccg     120
gcaagtggat ctactccaca gcagatcagg cccctccga agaggggcc tgatgcgtca      180 taggggacag gtagggaac tcaaccccg gctccttgct cgcgtcgggt catgccgtcc      240
gcgtacccct ccgcgtacct ggccctctcc cgttcctcga tctcggcggc gagctgatcg    300
cgcaggtgcg cctcc                                                     315

<210> SEQ ID NO 9
<211> LENGTH: 260
<212> TYPE: DNA
<213> ORGANISM: Micromonospora halophytica

<400> SEQUENCE: 9 tagggaatc cactccggag acgcccggag caatccggag catgacggag caaccagcag      60
gtcaggtggc ctgttgaccc cctgaccagg gccccggtac gggttcaatt cccatcagtc    120
accccaggta agaccaggt cagggccggt tctcaccggc cctgacgcat tttcaggggc    180
atggtggggg cgctaccggg ggtggggtgt ctcaccgcga gccagcatct cgatcaggcg    240
atcgagccgg cgctgccggg                                                260
```